United States Patent [19]

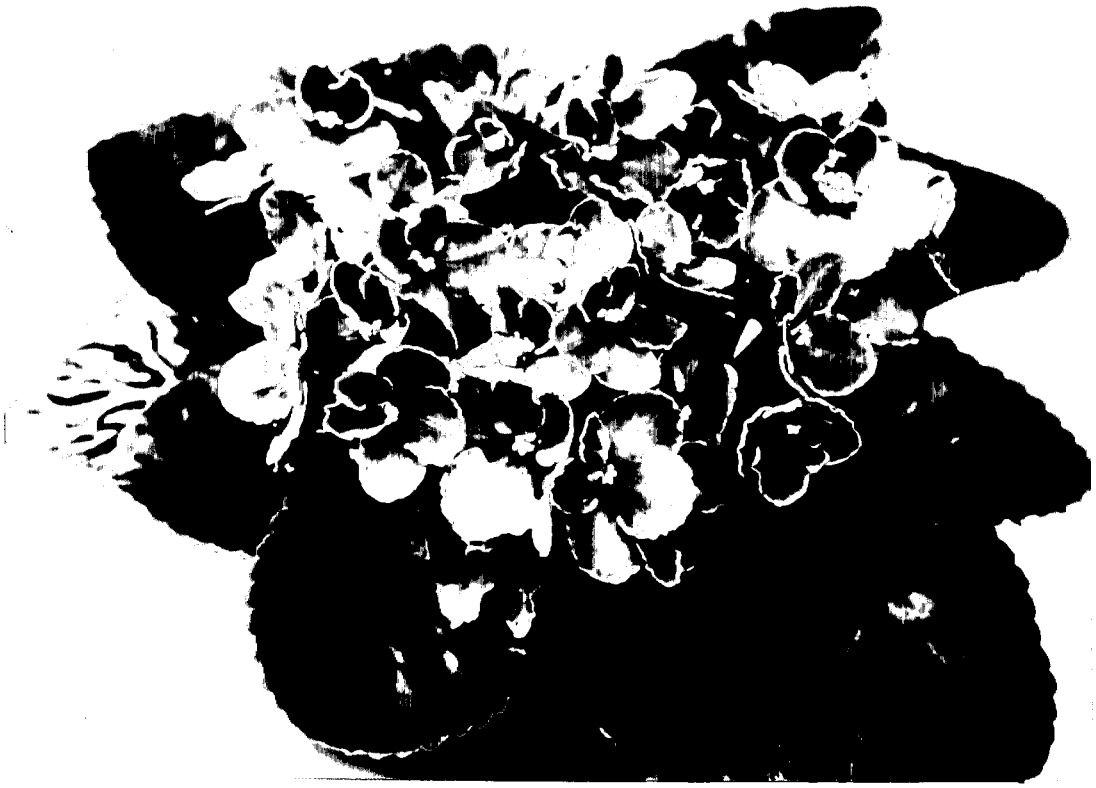

Holtkamp

[11] Patent Number: Plant 5,701

[45] Date of Patent: Mar. 25, 1986

[54] AFRICAN VIOLET PLANT NAMED MAUI

[75] Inventor: Reinhold Holtkamp, Isselburg, Fed. Rep. of Germany

[73] Assignee: Gessellschaftsvertrag uber die Ergindergemeinschaft "OPTIMARA", Fed. Rep. of Germany

[21] Appl. No.: 568,438

[22] Filed: Jan. 5, 1984

[51] Int. Cl.[4] ..... A01H 5/00

[52] U.S. Cl. ..... Plt./69

[58] Field of Search ..... Plt./69

*Primary Examiner*—Robert E. Bagwill

*Attorney, Agent, or Firm*—Schwartz, Jeffery, Schwaab, Mack, Blumenthal & Evans

[57] ABSTRACT

A new and distinct cultivar of African violet plant named Maui characterized by its relatively large dark lilac flowers with white edges, with the flowers being carried on strong flower stems; vigorous and uniform growth habit, dark green and serrated leaves, and by its floriferous habit, with a large and full bouquet of flowers being positioned centrally above the leaves.

1 Drawing Figure

1

The present invention comprises a new and distinct cultivar of African violet plant, botanically known as *Saintpaulia ionantha,* and named Maui.

The new cultivar was referred to during the breeding and selection process by the designation G 53/I, and is a product of a planned breeding program.

The new cultivar was originated from a cross made in a controlled breeding program in Isselburg, West Germany. The female, or seed parent was a cultivar designated AS 80 Blue Star White Edges. The male, or pollen parent was a cultivar designated Evelyn, a blue cultivar disclosed in U.S. Plant Pat. No. 4,154.

The new cultivar Maui was discovered and selected by me as a flowering plant within the progeny of the stated cross in a controlled environment in Isselburg, West Germany. Asexual reproduction of the new cultivar by leaf cuttings and by division of shoots, as performed by me at Isselburg, West Germany, has demonstrated that the combination of characteristics as herein disclosed for the new cultivar are firmly fixed and are retained through successive generations of asexual reproduction.

Maui has not been observed under all possible environmental conditions. The phenotype may vary significantly with variations in environment such as temperature, light intensity and day length. The following observations, measurements and values describe the new cultivar as grown in Isselburg, West Germany, and Nashville, Tenn. under greenhouse conditions which closely approximate those generally used in commercial practice.

The following traits have been repeatedly observed and are determined to be basic characteristics of Maui, which in combination distinguish this African violet as a new and distinct cultivar:

1. Vigorous growth habit.
2. Relatively large flowers which are dark lilac in color with white edges.
3. Strong flower stems, with the stems numbering 7-9 or more.
4. Attractive dark green shiny leaves, with serrated edges.
5. Uniform growth habit.
6. Very floriferous habit, with the strong and upright stems carrying up to 9 and more individual large single flowers.

2

The accompanying photographic drawing shows a typical specimen plant of the new cultivar. The colors appearing in the photograph are as true as possible with color illustrations of this type.

In the following description, color references are made to The Royal Horticultural Society Colour Chart (R.H.S.), except where general colors of ordinary significance are referred to. Color values were taken under natural light conditions at approximately mid-day in late November in Nashville, Tenn.

Botanical classification: *Saintpaulia ionantha,* Ramat. cv. Maui.

Parentage:

*Male parent.*—Evelyn, a blue cultivar disclosed in U.S. Plant Pat. No. 4,154.

*Female parent.*—AS 80 Blue Star White Edges.

Propagation: The new cultivar holds its distinguishing characteristics through successive propagations by leaf cuttings and by division of shoots.

Plant: From 8 cm. to 10 cm. tall when grown in pots, and approximately 25 cm. in diameter when fully grown.

Leaves:

*General form.*—Serrated heart shape.

*Diameter.*—65 mm.

*Texture.*—Leather-like.

*Aspect.*—Shiny.

*Veins.*—Light green, well pronounced underside.

*Color (upperside).*—Yellow green 147H.

*Color (underside).*—Red Purple 66C between the veins.

*Petiole.*—Brownish green.

Flowers:

*Buds.*—Ball shape.

*Sepals.*—Brown, spear shape. Calyx: Funnel shape. Aspect: Hairy. Peduncle: Short upright brownish green.

Individual flowers:

*Size.*—45-50 mm.

*Color.*—Upperside: Purple violet Group 81A with white edges. Underside: Purple violet Group 81C.

*Borne.*—On sturdy, upright flower stems.

*Shape.*—Violet shape, two small, three large petals; single flower form. Occasionally, flowers will have additional petals.

*Flowering time.*—8–10 weeks after potting to develop full maturity.

Reproductive organs:

*Anthers.*—Two, composed of four anther cells; seed capsules pushed slightly through.

*Styles.*—Dark purple; ovary is light green.

*Pollen color.*—Yellow.

*Roots.*—White when young and active; brownish when older.

*Disease resistance.*—Good as known to date.

General observations:

Maui has a vigorous and uniform growth habit. Strong and upright flower stems each carry up to 9 or more individual and large single flowers which are dark lilac in color with white edges. The leaves are relatively dark green with serrated edges, and provide an excellent contrast with the abundant, dark lilac flowers.

I claim:

1. A new and distinct cultivar of African violet plant named Maui, as illustrated and described, and particularly characterized by its relatively large dark lilac flowers with white edges, with the flowers being carried on strong flower stems; vigorous and uniform growth habit, dark green and serrated leaves, and by its floriferous habit, with a large and full bouquet of flowers being positioned centrally above the leaves.

* * * * *